(12) United States Patent
Santoro

(10) Patent No.: US 6,526,994 B1
(45) Date of Patent: Mar. 4, 2003

(54) MOTOR-DRIVEN APPARATUS FOR THE MECHANICAL CLEANING OF THE INTERDENTAL SPACES BY DENTAL FLOSS

(76) Inventor: Giovanni Santoro, Via Campodimele, 55, Rome (IT), 00189

( * ) Notice: Subject to any disclaimer, the term of this patent is extended or adjusted under 35 U.S.C. 154(b) by 0 days.

(21) Appl. No.: 09/889,622
(22) PCT Filed: Jan. 24, 2000
(86) PCT No.: PCT/IT00/00022
§ 371 (c)(1),
(2), (4) Date: Jul. 17, 2001
(87) PCT Pub. No.: WO00/44302
PCT Pub. Date: Aug. 3, 2000

(30) Foreign Application Priority Data

Jan. 26, 1999 (IT) .......................... RM99A0058

(51) Int. Cl.⁷ ................................. A61C 5/00
(52) U.S. Cl. ...................................... 132/322
(58) Field of Search ................ 132/322, 324, 132/325

(56) References Cited

U.S. PATENT DOCUMENTS

| | | | |
|---|---|---|---|
| 4,245,658 A | 1/1981 | Lecouturier | |
| 4,706,695 A | * 11/1987 | Urso | 132/322 |
| 5,207,773 A | * 5/1993 | Henderson | 132/322 |
| 5,217,031 A | 6/1993 | Santoro | 132/322 |
| 5,224,500 A | 7/1993 | Stella | 132/322 |

* cited by examiner

Primary Examiner—Cary E. O'Connor
(74) Attorney, Agent, or Firm—DeLio & Peterson, LLC; Anthony P. DeLio (57) ABSTRACT

An apparatus for the mechanical cleaning of the interdental spaces by dental floss comprising an outer holder containing a delivery reel of the fresh dental floss and a take-up reel of the worn-out dental floss, a drive mechanism for reciprocating the operating length of the dental floss between the arms of a fork to be positioned within the mouth in the interdental spaces, and a mechanism provided with friction device for rotating the delivery and take-up reels as well as the driving wheels transmitting the movement of the drive mechanism to the delivery and take-up reels, an outside case including the drive mechanism for the above-mentioned reciprocation and the power supply battery, a support base for two holders and a drive case carrying an induction coil for recharging the battery and including two sockets for holders.

8 Claims, 11 Drawing Sheets

MOTOR-DRIVEN APPARATUS FOR THE MECHANICAL CLEANING OF THE INTERDENTAL SPACES BY DENTAL FLOSS

The present invention relates to an apparatus for the mechanical cleaning of the interdental spaces by dental floss comprising an outer holder containing a delivery reel of the fresh dental floss and a take-up reel of the worn-out dental floss, means for reciprocating the operating length of the dental floss to be positioned within the mouth in the interdental spaces, and means provided with friction device for rotating the delivery and take-up reels as well as the driving wheels transmitting the movement of the drive means to the delivery and take-up reels, an outside case including the drive means for the above-mentioned reciprocation and the power supply battery, a support base for the rest and battery recharge positions of the holder and the drive case, respectively, also including one or more sockets for spare holders.

As known, it is very stringent to keep accurately clean the interdental spaces for the purpose of prevention of tooth decays and gum diseases. Presently, there are available on the market dental flosses that are inserted in each interdental space to perform their cleaning action and then are manually reciprocated by pulling and releasing a length of floss stretched between the hands of the user. There are also available fork frames to be manually moved, the dental floss being stretched between the two prongs of the fork like a hacksaw blade.

Beside being effective only if used carefully and patiently, such cleaning systems are not only unable to guarantee a rational use of the dental floss, some lengths of which are not conveniently used, but also are not easily or even laborious to use.

On the other hand, as far as the cleaning of teeth and gums is concerned, the problems connected to the use of the toothbrush, that is not satisfactory for the same reasons of not easy or even laborious use, have been solved to a great extent by the commercially available motor-driven toothbrushes. Therefore the applicant has sought to provide a motor-driven apparatus for the rational use of a dental floss for cleaning the interdental spaces so that the problems due to the manual use thereof are avoided.

To this end, the applicant has conceived an apparatus comprising an active unit consisting of a holder provided with a small-size fork-shaped head to be put into the oral cavity carrying a length of dental floss between its prongs, and mechanical means capable both of reciprocating such length of dental floss in the interdental spaces and traversing it little by little so that the worn-out length thereof, that is wound about a take-up reel, is little by little replaced by a length of fresh dental floss from a delivery reel while it is used.

The new features of the apparatus according to the invention are the use of a drive unit separated from the holder under rest conditions and quickly connected for the operation, and the use of non-rotatable guide members of the dental floss which allow a fork having prongs with reduced thickness comparable with the thickness of the manually operated forks to be used. Such fork allows also the innermost interdental spaces to be easily reached. In addition, the two reels for the delivery of the fresh dental floss and the take-up of the worn-out dental floss having a newly designed friction device are located side by side, which allows both the thickness of the holder to be reduced and the fresh length of dental floss to be separated from the worn-out length of dental floss, as recommended for hygiene purposes.

Further features of the invention will be more readily apparent from the following detailed description with reference to the accompanying drawings in which.

Figure 1:
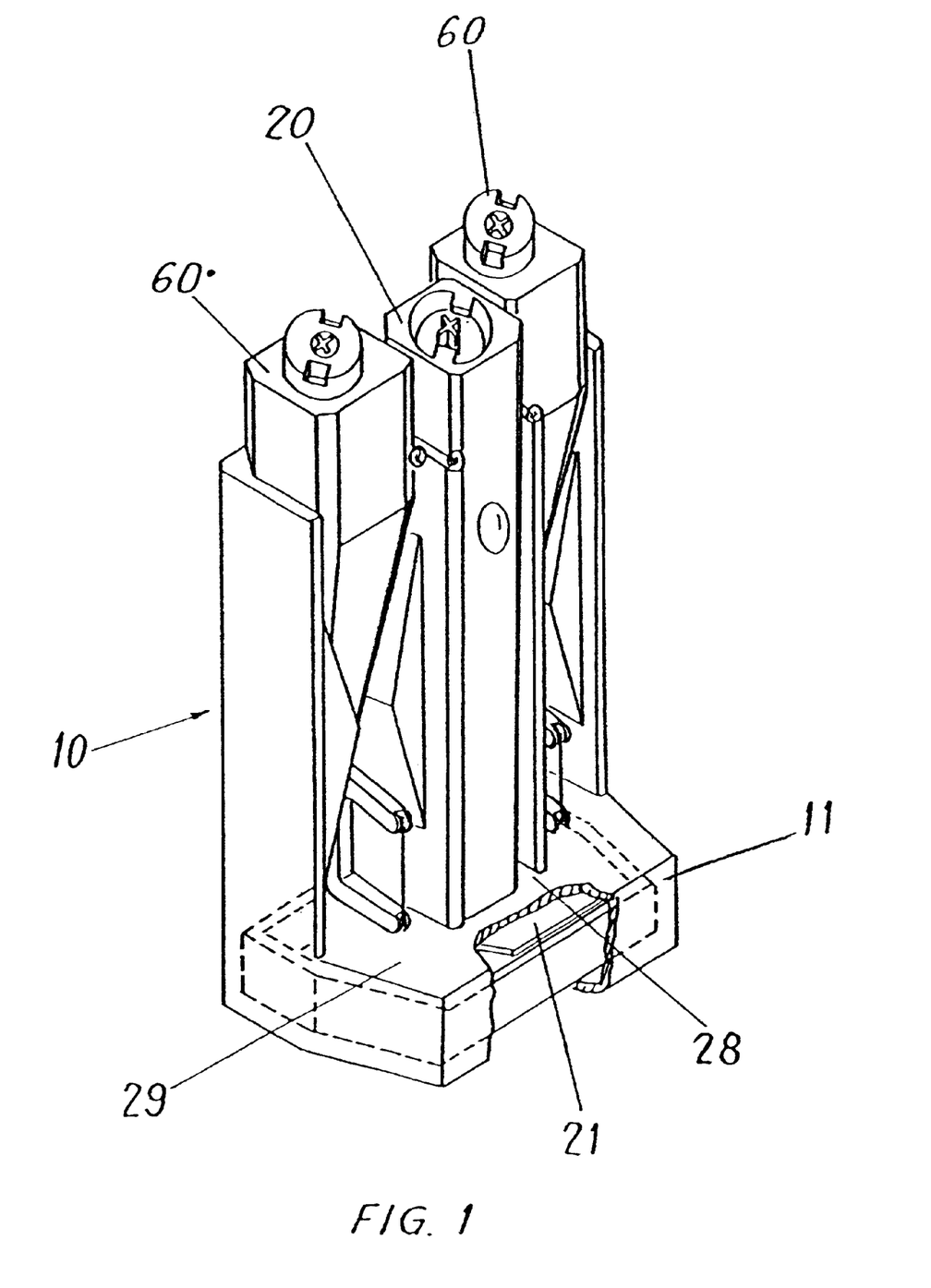
FIG. 1 is a perspective view of the apparatus in the rest condition placed on a support carrying two holders at both sides and a drive unit at the centre.
Figure 2:
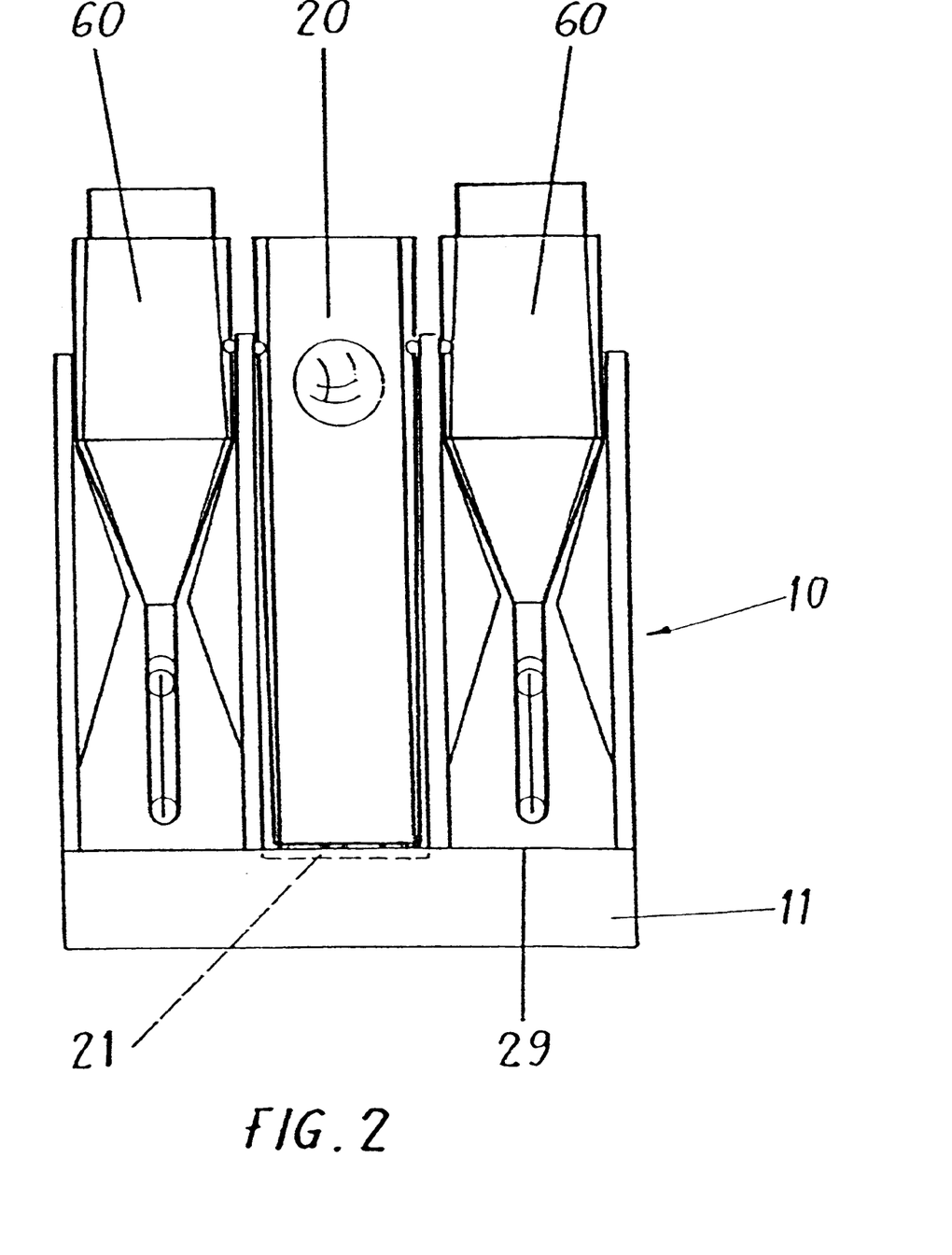
FIG. 2 is an front elevation view of the apparatus of FIG. 1.

FIGS. 1 and 2 show the invention in its general embodiment providing also a support 10 accommodating both a drive unit 20 and two holders 60 in addition to an apparatus provided with a drive unit indicated at 20 as described thereafter. These holders 60 include each a fork for stretching the length of dental floss to be used and for putting the same into the oral cavity between the interdental spaces, and also comprise all of the mechanical means for the reciprocation of such cleaning length of dental floss and its slow continuous motion for the replacement of the worn-out length with a length of fresh dental floss.

A coil 21 for recharging battery 22 of the drive unit by induction which energizes electric motor 23 driving the whole assembly, as described thereafter (FIGS. 1, 2, 5), is located under the upper plate 29 of base 11 of support 10 on which the lower face of the drive unit 20 rests.

Figure 5:
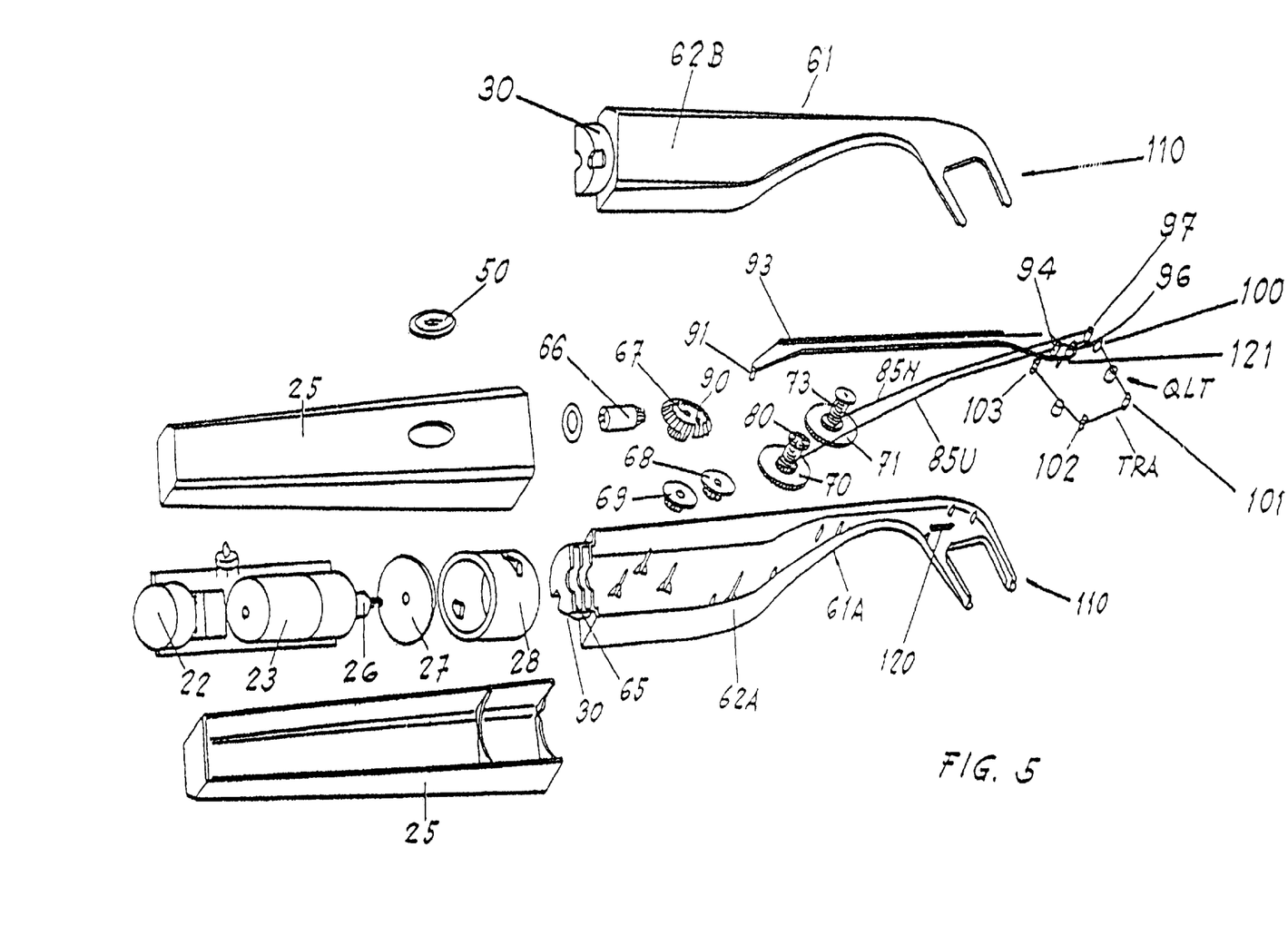
FIG. 5 is a perspective exploded view of the holder and drive unit of FIG. 3 opened to show the arrangement of the respective inside assembly.
Figure 6:
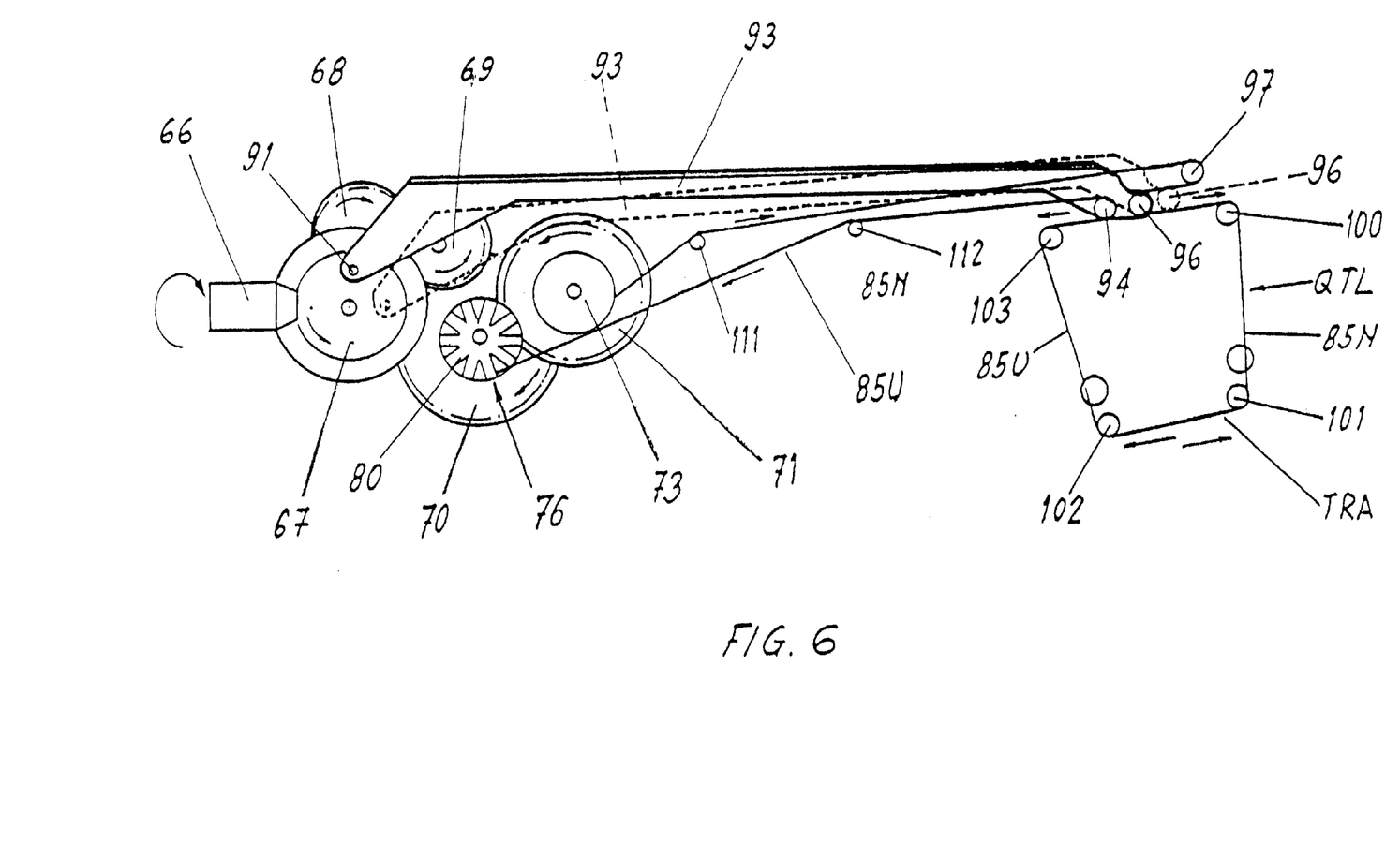
FIG. 6 is a perspective partial view showing in detail the delivery means, the take-up means, and the drive means of the dental floss in the two limit positions of the connecting rod-and-crank connection shown with solid and dashed lines, respectively.

It should be appreciated that the arrangement of two holders 60 in one unit in order to have a second holder of the disposable type in case the first holder is worn out together with a drive unit 20 with a rechargeable "for life" battery is very rational. A feature of the invention is the arrangement of the recharge system of battery 22 which is placed under area 28 of the base surface 29 of support 10 (FIGS. 1, 2 and 5). Actually, area 28 is perfectly flat without corners or recesses, which allows it to be easily and quickly cleaned.

Still with reference to FIG. 5 there is shown a drive unit 20 which is illustrated in section and includes two half shells 25, however, it consists of only one shell 25 containing electric motor 23, battery 22, and also electronic card 29 with recharge coil operating together with inductance plate 21.

Electric motor 23 has a drive shaft 26 which passes through sealing means consisting of perforated disc 27 and cylinder 28 and protrudes from drive unit 20 and engages pinion 66 rotating in sealing member 30 of case 65 of shell 30.

Figure 3:
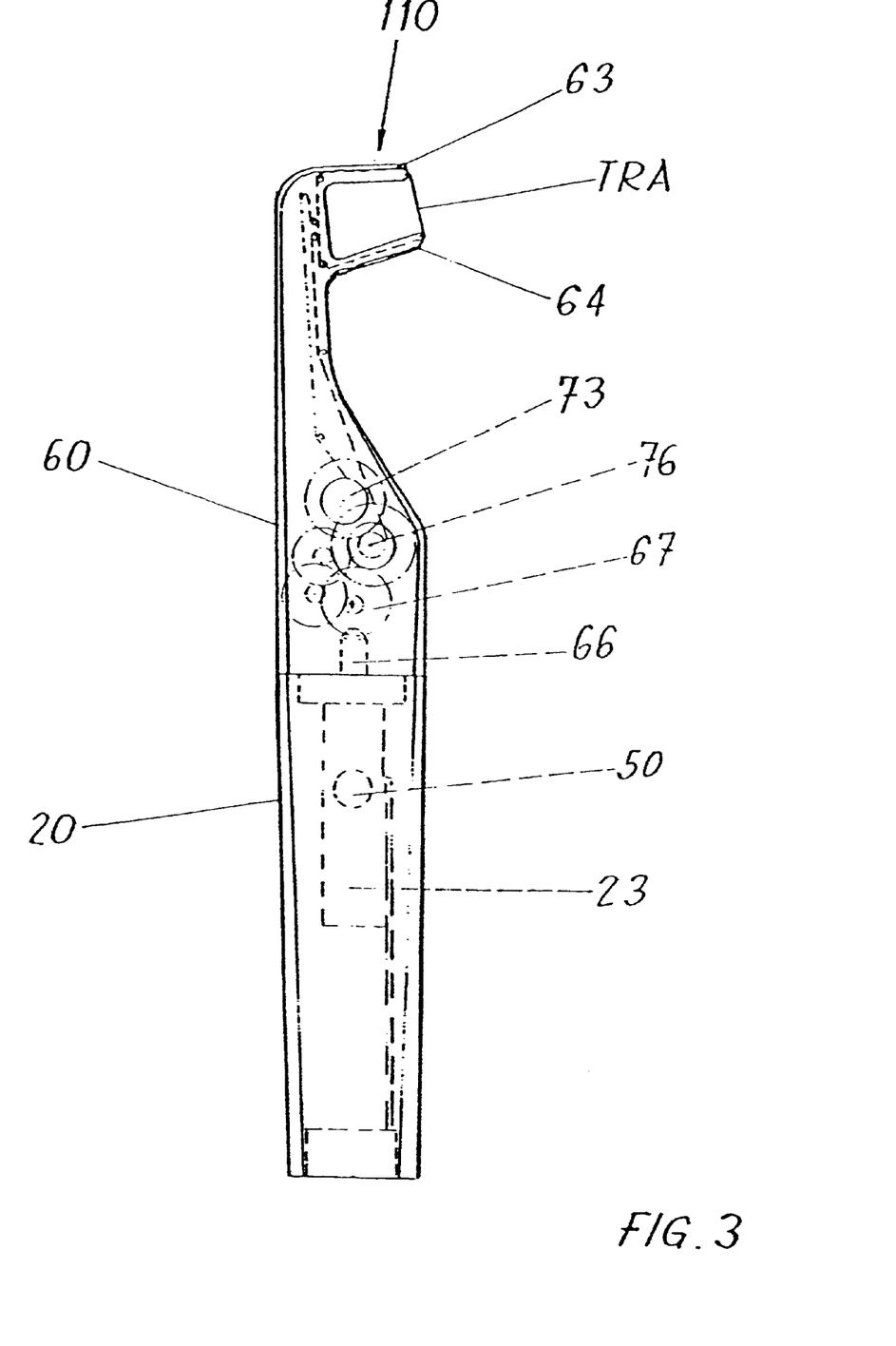
FIG. 3 is an outside view of the holder together with the drive unit connected thereto.

With reference now to FIGS. 3, 4(A, B, C, D) and 5 the portions included in motor-driven holder 60 for the use of a dental floss along with drive unit 20 and the relative kinematic members and supports will be described.

Figure 4A:
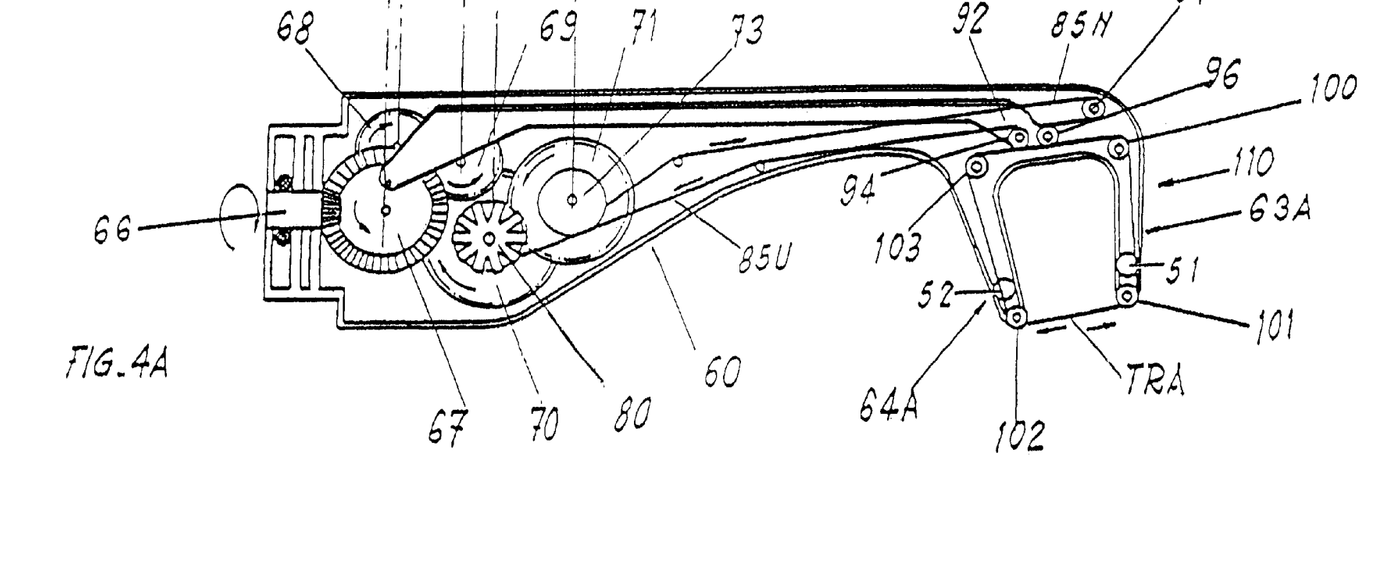
FIGS. 4A and 4B are 90° section views of the holder shown in FIG. 3.
Figure 4B:
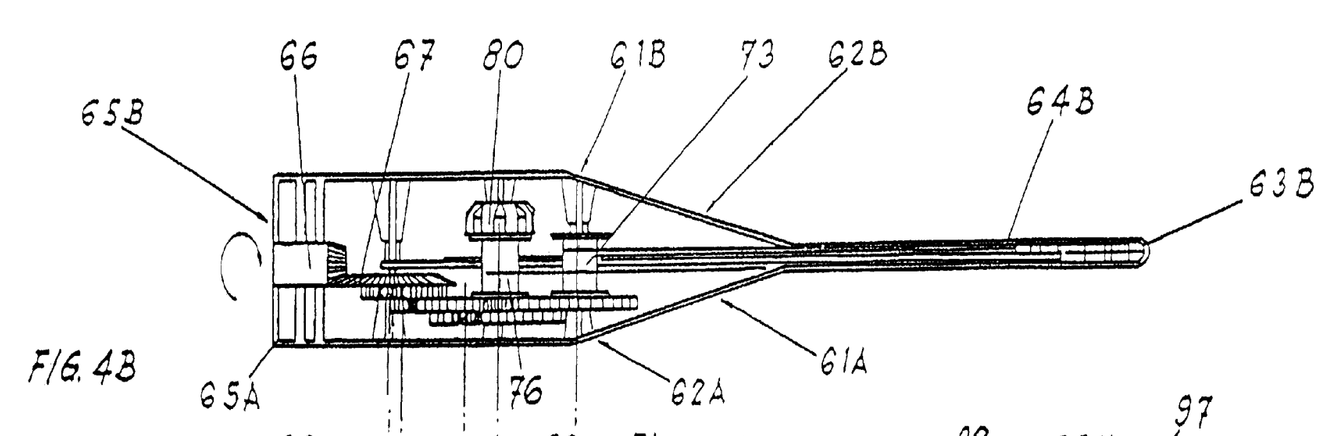

Referring to FIGS. 4A, 4B, motor-driven holder 60 consists of two mirror-like symmetrical half shells 61A and 61B, one of which includes the pins of all of the gears and the second includes the counteracting members which prevent the gears from sliding off the pins when the holder is used.

As can be seen in the Figures, each half shell 61A, 61B has a central body 62(A, B) tapering to the operating end of the holder and ending in a fork indicated at 110 with two prongs 63(A, B), 64(A, B), the opposite end being formed with a projecting housing 65(A, B) for pinion 66 forming a bevel gear pair along with double-toothed gear wheel 67.

Shell 61(A, B) formed as mentioned above includes (FIGS. 4C, 4D, 5) the following gearing meshed to one another: the above-mentioned bevel gear pair 66, 67 for transmitting the movement from the drive unit; a first double-toothed gear wheel 68, a second double-toothed gear wheel 69, a third double-toothed gear wheel 70, and a gear wheel 71.

Figure 4C:
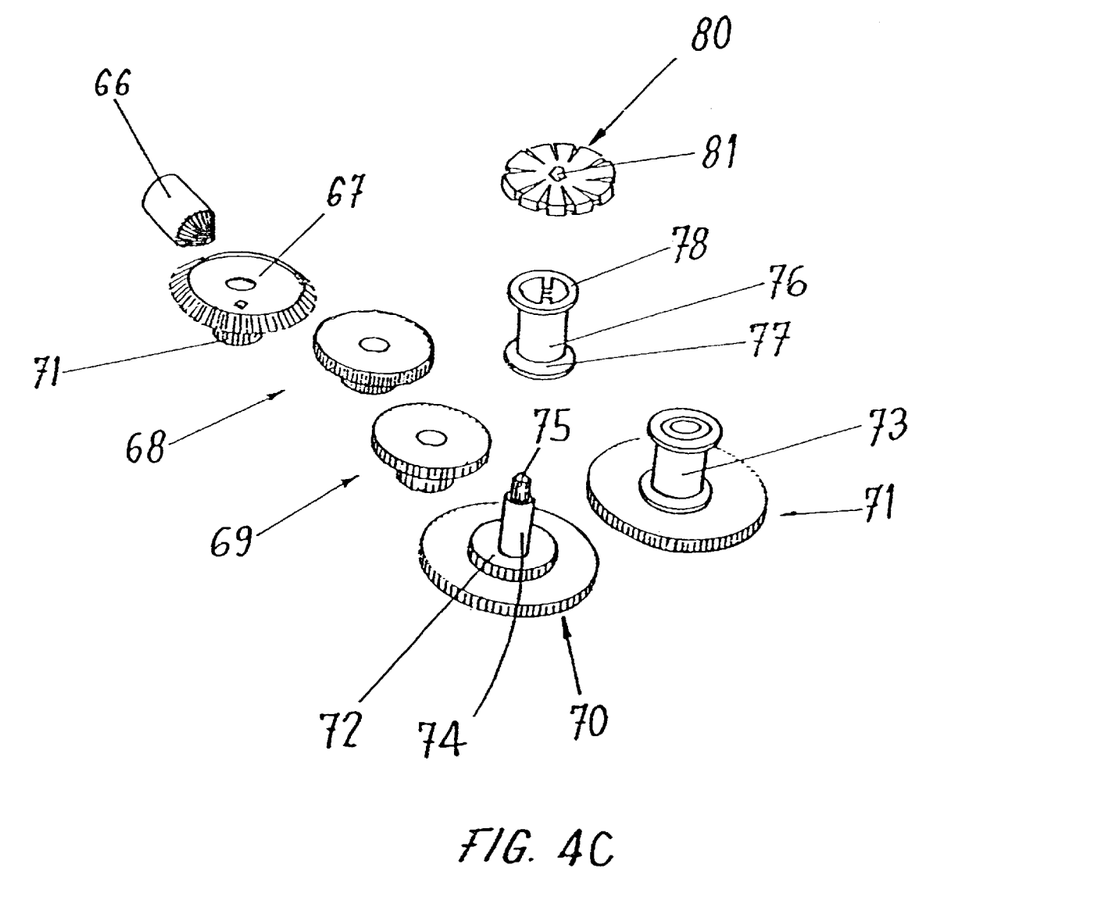
FIG. 4C is a fragmentary, exploded partial view of the train of gears offset in the vertical direction for driving the dental floss, and the two delivery and take-up reels of the dental floss.
Figure 4D:
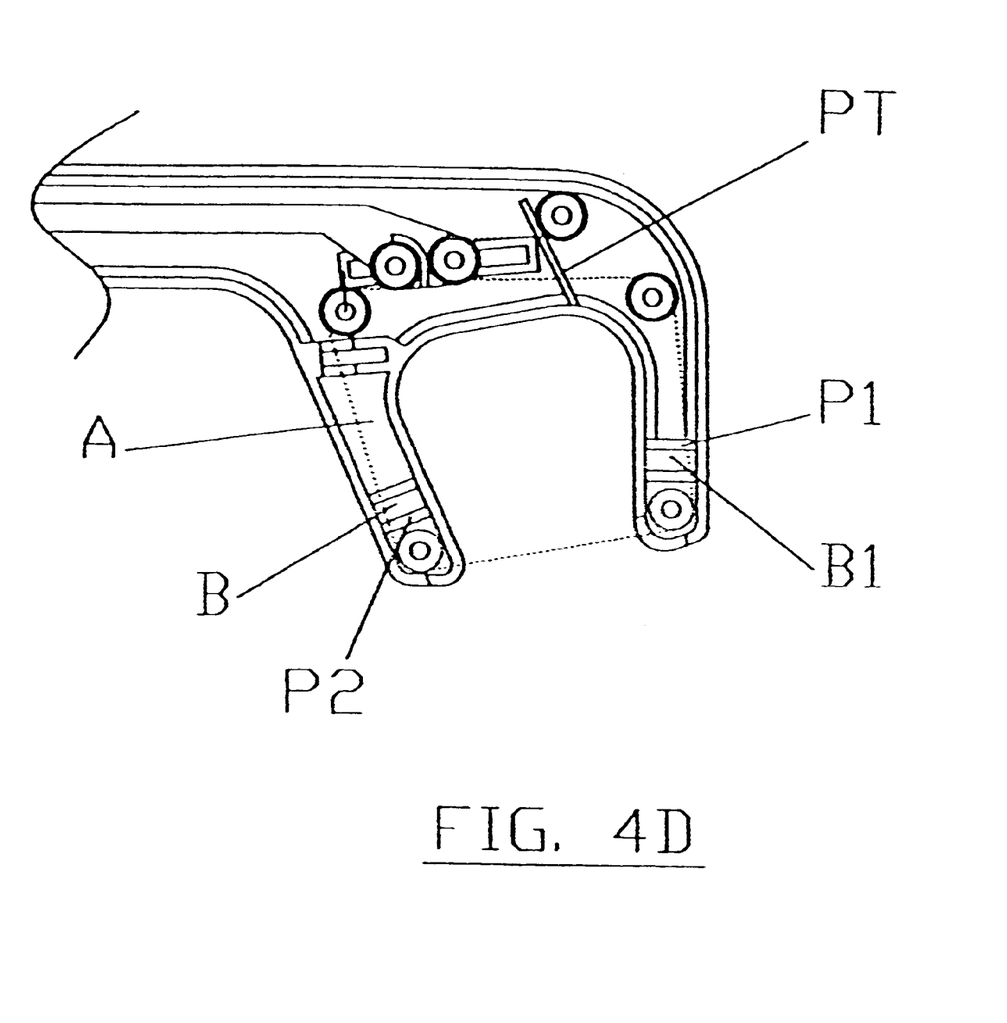
FIG. 4D shows the head of the apparatus provided with a chamber for the sterilisation of the worn-out dental floss.

Double-toothed gear wheels 68, 69 and 70 having upper and lower toothings of different diameters mesh to one another as shown in FIGS. 4C and 4D so that all together form a train of gears for the reduction of the rotation speed.

The first gear wheel 67 drives after one another the other gear wheels up to the last gear wheel 71. It should be appreciated that upon operation of the apparatus the rotation speed is reduced between the last two gear wheels of the train of gears. The double-toothed gear wheel 70 of such gear pair meshes to gear wheel 71 by its upper toothing 72 of smaller diameter so that gear wheel 71 rotates at lower speed than gear wheel 70.

Gear wheel 71 is integral with a cylindrical body 73 provided with upper and lower flanges and forming the delivery reel on which the fresh dental floss 85N is wound, and double-toothed gear wheel 70 is integral with a shaft 74 having an end 75 with a triangular (or polygonal) cross section. Shaft 74 carries take-up reel 76 of the worn-out dental floss 85U which has a lower flange 77 and an upper flange 78 and is idle mounted on such shaft.

Figure 8A:
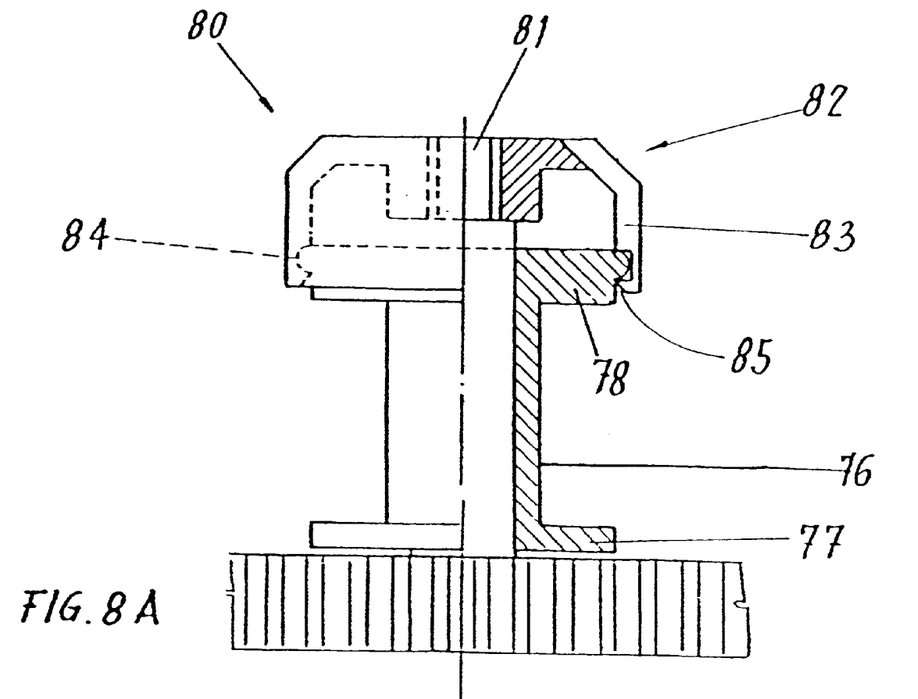
FIGS. 8A and 8B show in detail and in enlarged scale the friction device embodied in the take-up reel of the worn-out dental floss.
Figure 8B:
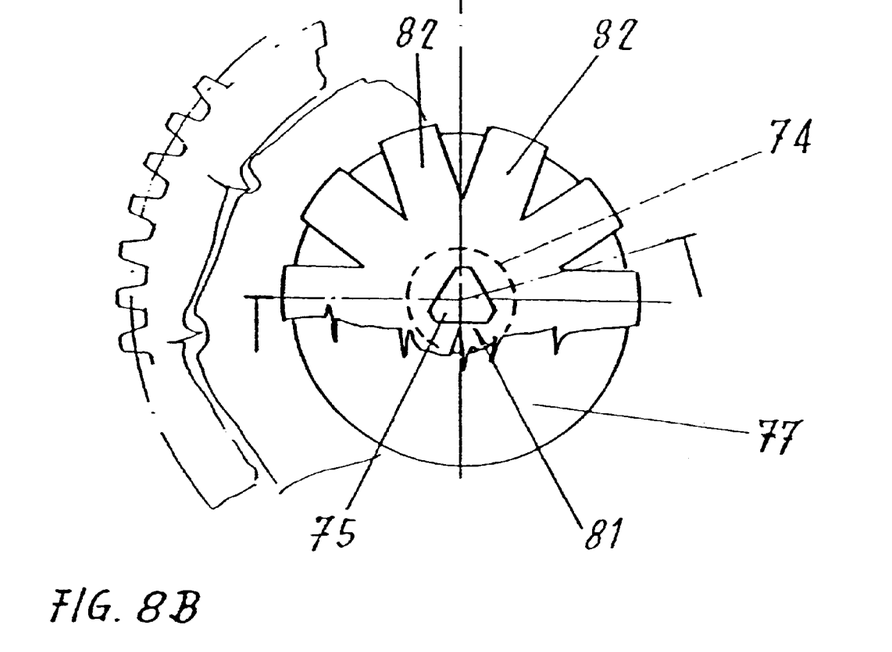
Figure 9:
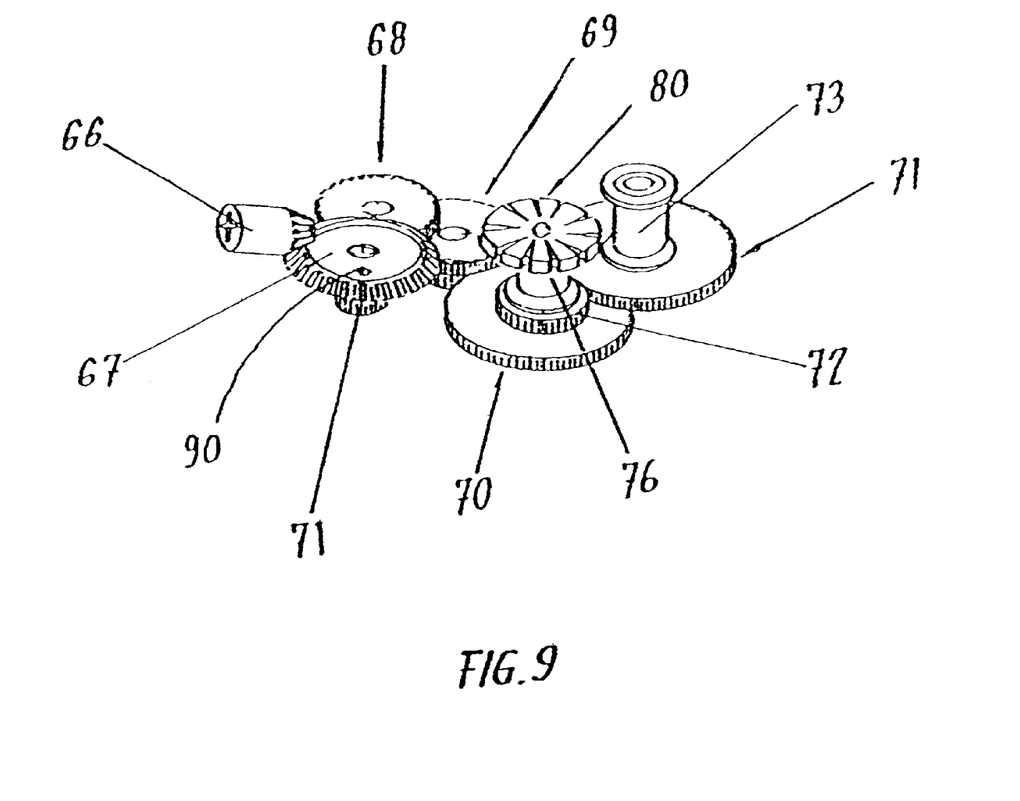
FIG. 9 is a partial view in enlarged scale of the train of gears meshed to one another of FIG. 4C.

Applied on the end 75 is a circular "cap" 80 of a suitable plastic material having a body provided with a central opening 81 with a shape complementary to s such end. Several arms 82 project from that body with a sunburst arrangement and are provided each with a flap 83 directed downwards (FIGS. 8A, 8B).

Each flap 83 has a slot 84 at its lower end bevelled at 85 so that all of the slots 84 along the periphery form together an annular discontinuous slot.

Cap 80 is snap fitted with its bevelling 85 into upper flange 78 of reel 76 (FIGS. 4C, 8A, 8B) which is received in the discontinuous annular slot 84. With such a construction the rotation of double-toothed gear wheel 70 is transmitted from the end 75 of shaft 74 to cap 80 keyed thereto because of the complementary shapes of such end and central opening 81, the cap transmitting such rotation by friction to upper flange 78 of reel 76. Said construction, the inherent elasticity of arms 82 of plastic material, and the friction contact between such arms and flange 78 allow a transmission of the movement with slippage from cap 80 integral with shaft 74 to double-toothed gear wheel 70 and the cylindrical body of reel 76.

The requested movement of the dental floss is determined by the kinematics of the apparatus starting from gear wheel 67 having an eccentric hole 90 in which a pin 91 integral with one end of an elongated connecting rod 93 is inserted. Two idle little wheels 94, 96 aligned side by side are supported at the opposite end 92 of the connecting rod (FIG. S). Furthermore, further four idle small wheels indicated at 100, 101, 102, 103 are disposed inside fork 110 of holder 60 at the four corners of a quadrilateral at the ends of arms 63, 64. Wheel 97 is idle supported outside such quadrilateral and wheels 101 and 102 are located in front of each other at the ends of arms 63, 64 of fork 110, respectively. The operating length of the dental floss TRA extends about the latter wheels. With reference to quadrilateral QLT formed by dental floss 85N, 85U, as better described thereafter, the small wheels described above cause the operating length TRA of the dental floss extending between the ends of arms 63, 64 of fork 110 to reciprocate.

For a better understanding of the operation of the apparatus it should be noted that the dental floss has two lengths, and namely the length of fresh dental floss 85N extending from reel 73 to operating length TRA of quadrilateral QLT and the length of worn-out dental floss 85U extending from such length TRA and reel 76 of the worn-out dental floss.

Figure 7A:
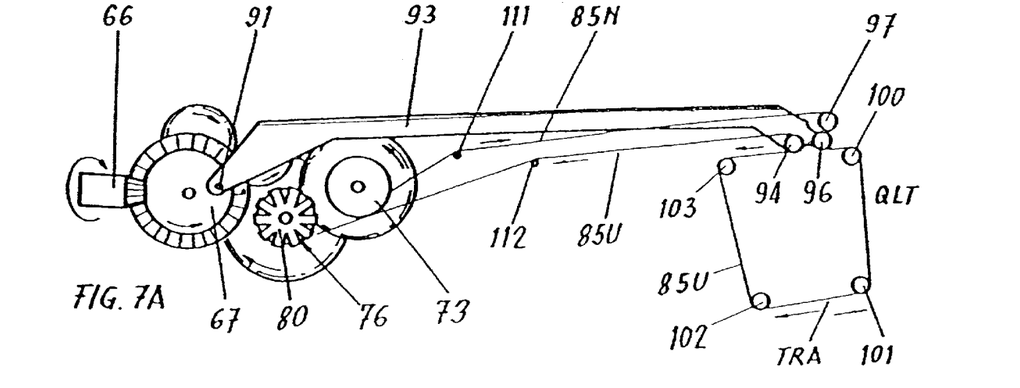
FIGS. 7A, 7B and 7C are perspective partial views similar to FIG. 6 of the same members in three different positions of their operation, i.e. the two limit positions and an intermediate positions.
Figure 7B:
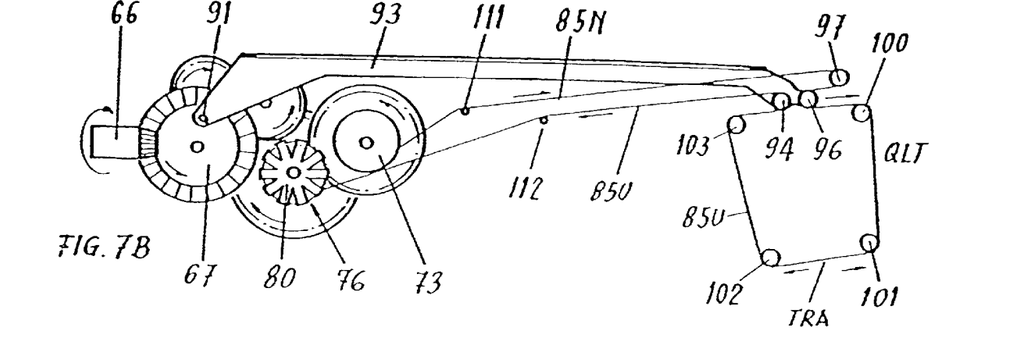
Figure 7C:
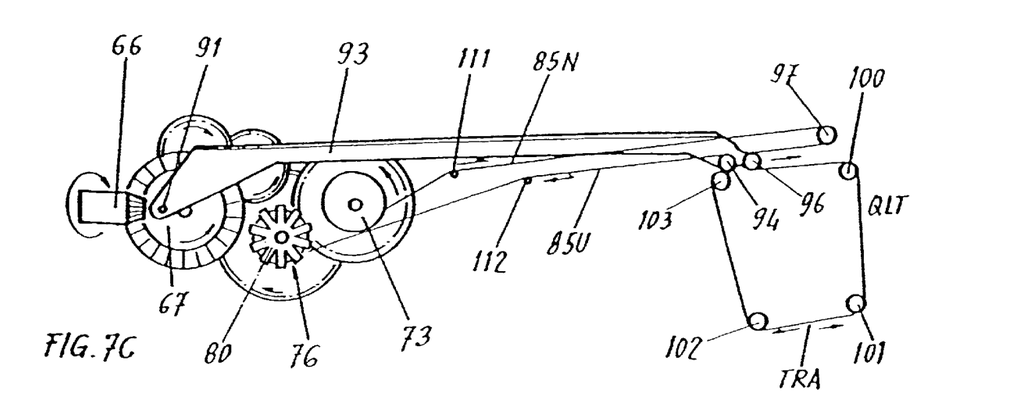

In its path the length of fresh dental floss 85N is guided by pin 111, turns by 180° first about wheel 97 and then about wheel 96 idle supported by connecting rod 93, and is then deviated by 900 by small wheels 100 and 101. On the other hand, worn-out dental floss 85U is deviated by 90° after the operating length TRA by small wheels 102 and 103 and turns by 180° about wheel 94 located side by side to wheel 96 which is also idle supported on connecting rod 93, and then is guided by pin 112 and is wound about reel 76 of worn-out dental floss 85U (FIGS. 7A, B, C).

With such an arrangement the operation of the apparatus according to the invention is as follows. Once drive unit 20 and one holder 60 are removed from support base 10 and assembled together, and fork 110 is put into the oral cavity with length TRA of the dental floss positioned in the selected interdental space, button switch 50 is depressed for energizing motor 23 that will rotate the whole train of gears by bevel gear pair 66–67. As described, connecting rod 93 is reciprocated because of its connection to gear wheel 67 via pin 91, and the pair of small wheels 94 and 96 are also reciprocated so as to be moved to and away both from small wheels 100, 103 and small wheel 97. Such a movement causes the sides of quadrilateral QRT to be alternately driven, particularly length TRA carrying out the cleaning action of the interdental space. It should be appreciated that any linear alternate movement of wheel pair 94, 96 in both directions relative to two lengths of dental floss between wheel pairs 97–96 and 96–100, 103–94 and 94–76 causes a double as long shift of length TRA.

Such an alternate movement of length TRA, as already mentioned, is the cleaning movement of the selected interdental space.

Thus, the alternate movement of length TRA of the dental floss should be added to the continuous movement of the dental floss allowing the slow, continuous replacement of such length with fresh dental floss 85N from reel 73 as the length of worn-out dental floss 85U is wound about reel 76 of worn-out dental floss 85U.

Such necessary replacement is automatic because of the angular speed of reel 76 of worn-out dental floss 85U which is greater than that of reel 73 of fresh dental floss 85N, as already described.

Consequently, reel 76 "ask " for more dental floss than reel 73 can deliver so that a traction on the whole (fresh 85N, worn-out 85U) dental floss is generated causing a torque to be applied to reel 76 which in turn causes a slipping of cap 80 of friction device relative to upper flange 78 of reel 76.

As far as the hygiene conditions of the apparatus according to the invention is concerned, it should be appreciated that a dental floss impregnated by bactericidal or bacteriostatic substances may also be used in addition to the separation of the lengths of fresh and worn-out dental flosses.

Felt pads 51, 52 may also be impregnated with the same bactericidal substances. They are stuck to the inside of arms 63(A, B)–64(A, B) of holder 60 and form the sealing means against the penetration of liquids into holder 60. As far as the rear portion of the latter is concerned, the sealing is ensured by perforated disc 27 and cylinder 28 with O-ring mentioned above.

As for the dental floss, a different colour is provided for the "head" and the "tail", on one hand, for ensuring that the dental floss is absolutely fresh and, on the other hand, for warning that it is about to finish. The relative colours may be green and red, respectively.

Still as far as the hygiene condition of the apparatus is concerned, FIG. 4D shows a possible solution in which arm 64 of the fork includes a chamber A crossed by the worn-out dental floss entering back the apparatus, in which chamber a gel of a bactericidal substance is contained, preferably chlorexidine, potassium nitrate, potassium salts of glyciretinic acid. This ensures that the worn-out dental floss does not carry bacteria into the apparatus which are capable of contamination of the fresh dental floss. References B and B1 indicate filtering felt pads, and references P1 and P2 indicate sealing baffles of the felt pads while PT indicates a separation baffles.

I claim:

1. An apparatus for the mechanical cleaning of the interdental spaces by dental floss comprising an outer holder containing a delivery reel of the fresh dental floss and a take-up reel of the worn-out dental floss, drive means for reciprocating the operating length of the dental floss between the arms of a fork to be positioned within the mouth in the interdental spaces, and means provided with friction device and including a bevel gear pair for rotating the delivery and take-up reels as well as driving gear wheels for transmitting the movement of the drive means to the delivery and take-up reels, an outside case including the drive means for the above-mentioned reciprocation and a power supply battery, a support base for the rest and battery recharge positions of the holder and the drive case, respectively, also including one or more sockets for spare holders, said drive means including a connecting rod reciprocated by said bevel gear pair, characterized in that the apparatus includes two small wheels for the reciprocation of the operating length of the dental floss operating together with similar small wheels located in said case, the two smaller wheels being disposed side by side on said connecting rod in order to avoid any possible contact of bacterial contamination between the length of fresh dental floss and the length of worn-out dental floss which are kept separated.

2. The apparatus according to claim 1, wherein the difference of angular speed between said delivery reel of fresh dental floss and said take-up reel of worn-out dental floss causes a traction ensuring the requested slow, continuous replacement of the operating length of the dental floss while it is used.

3. The apparatus according to claim 2, wherein said take-up reel of the worn-out dental floss, supported by a double-toothed gear wheel and rotating at an angular speed greater than that of the gear wheel driving the delivery reel of the fresh dental floss, is rotated through a friction device slipping by friction.

4. The apparatus according to claim 3, wherein said friction device includes a shaft with polygonal end which is integral with said double-toothed gear wheel so as to rotate at the same speed, a sleeve forming the body of said reel and having a lower flange and an upper flange, and a circular cap provided with a central opening having a shape complementary to said end of the shaft so that it is keyed thereon, and with several arms having a sunburst arrangement and such a shape as to surround said flange and to hold it tightly by a sufficient force to allow a relative rotation by friction and to produce a slow motion by friction.

5. The apparatus according to claim 1, wherein a felt pad is placed within each said arm of said fork through which the dental floss slides tightly like a "sandwich" at the entrance and at the output of the apparatus upstream and downstream of said operating length of the dental floss in order to prevent liquids from entering the apparatus.

6. The apparatus according to claim 1, wherein said battery inside said case is charged by induction through a plate beneath the portion of the base to surface free of corners or recesses bearing said case under rest condition, the corresponding wall of the outside shell of said case bearing on said portion of the base surface, the battery being charged by an electronic card through said induction plate.

7. The apparatus according to claim 1, wherein the dental floss includes head and tail length, said head and tail lengths of the dental floss in the delivery reel having different colours in order to ensure that it has not still been used and to warn that it is about to finish, respectively.

8. The apparatus according to claim 7, wherein said dental floss, upon entering the apparatus, crosses a chamber containing a bactericidal, antifermentative gel.

\* \* \* \* \*

UNITED STATES PATENT AND TRADEMARK OFFICE
CERTIFICATE OF CORRECTION

PATENT NO.   : 6,526,994 B1
DATED        : March 4, 2003
INVENTOR(S)  : Giovanni Santoro

It is certified that error appears in the above-identified patent and that said Letters Patent is hereby corrected as shown below:

<u>Column 3,</u>
Line 48, delete "s such end" and substitute therefor -- such end --.

<u>Column 4,</u>
Line 7, delete "Fig. S" and substitute therefor -- Fig. 5 --.
Line 27, delete "900" and substitute therefor -- 90° --.

Signed and Sealed this

Twenty-ninth Day of July, 2003

JAMES E. ROGAN
*Director of the United States Patent and Trademark Office*